(12) United States Patent
Chou et al.

(10) Patent No.: US 9,121,822 B2
(45) Date of Patent: Sep. 1, 2015

(54) PORTABLE BIOCHEMICAL TESTING APPARATUS OPERATING METHOD

(71) Applicant: Crystalvue Medical Corporation, Gueishan, Taoyuan (TW)

(72) Inventors: Chung-Cheng Chou, Taoyuan (TW); William Wang, Taoyuan (TW)

(73) Assignee: Crystalvue Medical Corporation, Taoyuan (TW)

( * ) Notice: Subject to any disclaimer, the term of this patent is extended or adjusted under 35 U.S.C. 154(b) by 269 days.

(21) Appl. No.: 13/942,379

(22) Filed: Jul. 15, 2013

(65) Prior Publication Data

US 2013/0313114 A1    Nov. 28, 2013

Related U.S. Application Data

(62) Division of application No. 13/190,602, filed on Jul. 26, 2011, now Pat. No. 8,562,912.

(30) Foreign Application Priority Data

Jul. 30, 2010   (TW) ................................ 99125279 A

(51) Int. Cl.
*G01N 21/01* (2006.01)
*G01N 27/447* (2006.01)

(52) U.S. Cl.
CPC .................................... *G01N 27/447* (2013.01)

(58) Field of Classification Search
None
See application file for complete search history.

(56) References Cited

PUBLICATIONS

Hwang, H. et al. Enhanced discrimination of normal oocytes using optically induced pulling-up dielectrophoric force, 2009, Biomicrofluidics, vol. 3, pp. 014103-1-014103-10.

*Primary Examiner* — Robert Xu
(74) *Attorney, Agent, or Firm* — Patterson & Sheridan, LLP

(57) ABSTRACT

A method of operating a portable biochemical testing apparatus is disclosed. The portable biochemical testing apparatus includes a light source module, a sample module, a photoconductive material layer, a touch module, and a control module. At least one sample is disposed in the sample module. The photoconductive material layer is disposed between the sample module and the light source module. The touch module generates a driving signal according to a touch action of the user to drive the light source module to emit a light. When the light is emitted to the photoconductive material layer, the photoconductive material layer will generate a photoelectric driving effect. The at least one sample is affected by the photoelectric driving effect and generates a change corresponding to the touch action.

5 Claims, 5 Drawing Sheets

PORTABLE BIOCHEMICAL TESTING APPARATUS OPERATING METHOD

CROSS-REFERENCE TO RELATED APPLICATIONS

This application is a divisional of U.S. patent application Ser. No. 13/190,602, entitled "PORTABLE BIOCHEMICAL TESTING APPARATUS AND OPERATING METHOD THEREOF", filed Jul. 26, 2011, which claims priority to Taiwan Patent Application Serial Number 099125279, filed Jul. 30, 2010, both of which are herein incorporated by reference.

BACKGROUND OF THE INVENTION

1. Field of the Invention

The invention relates to biochemical test, in particular, to a method of operating a portable biochemical testing apparatus having small size and the portable biochemical testing apparatus is easy for the user to control samples through a touch way.

2. Description of the Prior Art

In recent years, with the continuous progress of biotechnology, the importance of the biochemical testing region has been gradually increased. Therefore, various kinds of biochemical testing apparatuses are shown in the market.

However, these conventional biochemical testing apparatuses are often large and weighty, so that they can only be disposed at a certain position. It is hard for the user to move or carry them to other places. Therefore, the user must go to the place that the biochemical testing apparatus is disposed to use it. It is inconvenient for the user and the usage of the biochemical testing apparatus has been largely limited.

In addition, when the user uses the conventional biochemical testing apparatus to observe and control the samples, because the limitation of the biochemical testing apparatus itself, the user can only observe the samples in a limited field, and it is inconvenient for the use to control the samples.

Therefore, the invention provides a portable biochemical testing apparatus operating method thereof to solve the above-mentioned problems.

SUMMARY OF THE INVENTION

An embodiment of the invention is a portable biochemical testing apparatus operating method. In this embodiment, the portable biochemical testing apparatus operating method is applied in a portable biochemical testing apparatus. The portable biochemical testing apparatus includes a light source module, a sample module, a photoconductive material layer, a display module, a touch module, and a control module, wherein at least one sample is disposed in the sample module, a specific sample of the at least one sample is located at a first sample position of the sample module, and the photoconductive material layer is disposed between the sample module and the light source module. The display module is disposed above a top surface of the sample module and used to display the at least one sample disposed under the display module. The specific sample is displayed at a first display position of the display module corresponding to the first sample position of the sample module. The touch module is disposed above the top surface of the sample module and overlapping the display module.

The portable biochemical testing apparatus operating method includes steps of: (a) the display module is disposed above a top surface of the sample module and used to display the at least one sample disposed under the display module, the specific sample is displayed at a first display position of the display module corresponding to the first sample position of the sample module, the touch module is disposed above the top surface of the sample module and overlapping the display module; (b) the control module generating a driving signal to the light source module according to the touch command to drive the light source module to emit a light; (c) when the light is emitted to the photoconductive material layer, the photoconductive material layer generating a photoelectric driving effect; and (d) the photoelectric driving effect affecting the specific sample to move from the first sample position of the sample module to a second sample position of the sample module corresponding to the second display position of the display module.

In practical applications, the photoconductive material layer and the sample module are integratedly designed, and the photoconductive material layer is disposed under the at least one sample. In addition, the portable biochemical testing apparatus can further include a bearing module disposed between the sample module and the light source module. The photoconductive material layer and the bearing module are integratedly designed, and the photoconductive material layer is disposed under the sample module. The at least one sample disposed in the sample module can be disposable or cleanable, the sample module replaces each of the at least one sample respectively through an extraction way. The light source module can include a changeable light source unit or a multi-band light source unit, and the photoelectric driving effect is an electrophoresis (EP) mechanism or a dielectrophoresis (DEP) mechanism.

Compared to the prior arts, the portable biochemical testing apparatus operating method thereof in the invention can not only provide the user the effect of easy control and observation through the design of touch interface, but also effectively shrink the volume and size of the portable biochemical testing apparatus through the photoelectric driving theorem, so that the user can carry or move the portable biochemical testing apparatus more easily. In addition, the removable sample module of the portable biochemical testing apparatus of the invention can be intergratedly designed with the photoconductive material layer, so that it can provide a sample bearing function and a sample driving function at the same time. Furthermore, the portable biochemical testing apparatus of the invention can test many sample modules at the same time, and provide the functions of changeable light source and multi-band light source.

Above all, the portable biochemical testing apparatus operating method thereof in the invention can effectively solve the problems of the conventional biochemical testing apparatus including being large and weighty, hard to be carried and moved, small sample observation field, hard to be controlled for the user, therefore, it has great market potential in the future.

The advantage and spirit of the invention may be understood by the following detailed descriptions together with the appended drawings.

BRIEF DESCRIPTION OF THE APPENDED DRAWINGS

DETAILED DESCRIPTION OF THE INVENTION

Figure 1:
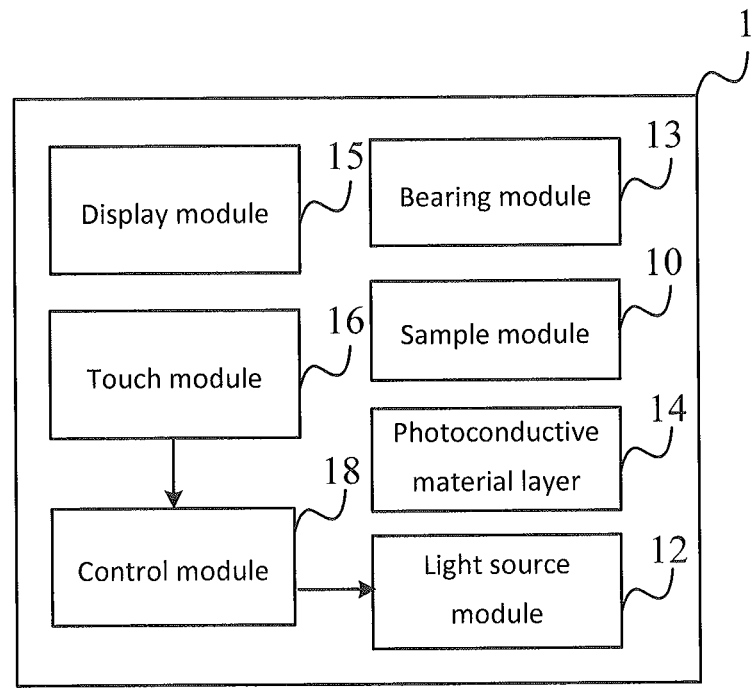
FIG. 1 illustrates a functional block diagram of the portable biochemical testing apparatus of an embodiment in the invention.

An embodiment of the invention is a portable biochemical testing apparatus. In this embodiment, the portable biochemical testing apparatus is used to perform a procedure of test and observation to at least one sample. In fact, the at least one sample can be any kinds of biological samples or chemical samples without any limitations. Please refer to FIG. 1. FIG. 1 illustrates a functional block diagram of the portable biochemical testing apparatus.

As shown in FIG. 1, the portable biochemical testing apparatus 1 includes a sample module 10, a light source module 12, a bearing module 13, a photoconductive material layer 14, a display module 15, a touch module 16, and a control module 18. Wherein, the control module 18 is coupled to the light source module 12 and the touch module 16 respectively. In this embodiment, the at least one sample is disposed in the sample module 10; the photoconductive material layer 14 is disposed between the sample module 10 and the light source module 12.

Figure 2:
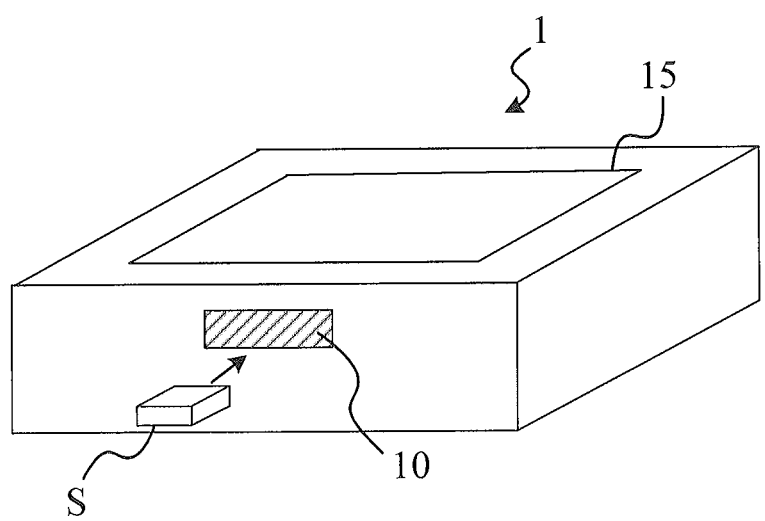
FIG. 2 illustrates an exterior view diagram of the portable biochemical testing apparatus of an embodiment in the invention.

Then, please refer to FIG. 2. FIG. 2 illustrates an exterior view diagram of the portable biochemical testing apparatus 1. As shown in FIG. 2, the display module 15 is disposed on a top surface of the portable biochemical testing apparatus 1 and used to display the image of the at least one sample for the user to observe. When the user wants to test the sample, all he/she has to do is to put the sample in the sample module 10.

It should be noticed that the sample module 10 is designed as a removable cassette. Because the sample is disposable or cleanable, when the user wants to use another sample to replace the original sample, all he/she has to do is to extract the original sample and put another sample into the sample module 10. It is very convenient for the user to use.

In this embodiment, the touch module 16 generates a touch command according to a touch action of the user on the display module 15. In fact, the touch module 16 can include an image sensing unit. The image sensing unit is used to sense the touch action of the user generated on the display module 15 and generate the touch command accordingly. In fact, the touch action can be a touch, a movement, a rotation, a dragging, or any other types of action without any limitations.

Then, the control module 18 generates a driving signal to the light source module 12 according to the touch command to drive the light source module 12 to emit a light. In practical applications, the light source module 12 can include a plurality of light source units 120 (see FIG. 5A). The plurality of light source units 120 can be any types of light source emitting apparatuses, such as conventional bulbs, fluorescents, or LEDs, and the number and the positions of the light source units 120 can be determined based on practical needs without any limitations.

In addition, the control module 18 can generate corresponding driving signals to the light source module 12 according different touch commands to control a part of light source units 120 or all light source units 120 of the light source module 12 to light. For example, when the control module 18 receives a first touch command, the control module 18 will drive the left part of light source units 120 of the light source module 12 to light according to the first touch command; when the control module 18 receives a second touch command, the control module 18 will drive the right part of light source units 120 of the light source module 12 to light according to the second touch command, but not limited to this case.

When the light is emitted to the photoconductive material layer 14, the photoconductive material layer 14 will generate a photoelectric driving effect. In practical applications, the photoelectric driving effect can be an electrophoresis (EP) mechanism, a dielectrophoresis (DEP) mechanism, or any other mechanisms of providing electric field change and/or magnetic field change through electrodes.

The definition of the so-called "EP mechanism" is that under the electric field, the charged particles will move toward the electrode with opposite electricity. For example, under the electric field, the positive charge will move toward the negative electrode, and the negative charge will move toward the positive electrode.

The so-called "DEP mechanism" means the phenomenon that the particle moves under the non-uniform electric field. When the particle is polarized under the non-uniform electric field, the particle will be affected by an asymmetric electric field attraction to move toward a direction of strong electric field or weak electric field. In fact, the DEP mechanism can be used to control any charged or uncharged particles, the small substance such as cells, bacteria, proteins, DNAs, or Carbon nanotubes.

Figure 3A:
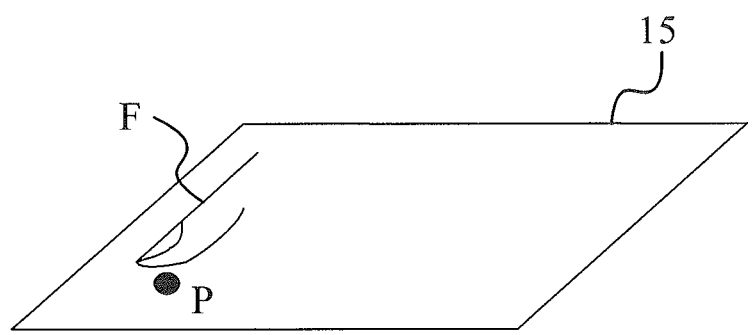
FIG. 3A and FIG. 3B illustrate the user controlling the samples in the portable biochemical testing apparatus through a touch way.
Figure 3B:
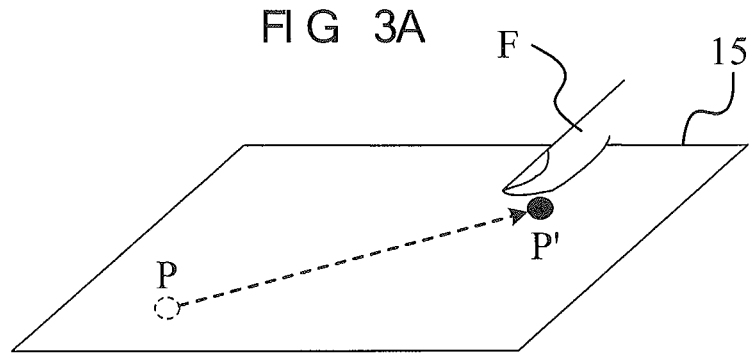

After the photoconductive material layer 14 generates the photoelectric driving effect, the at least one sample will be affected by the photoelectric driving effect and generate a change corresponding to the touch action. In practical applications, as the above-mentioned DEP mechanism used to control the small substance, the at least one sample will be affected by the EP mechanism or the DEP mechanism to generate the change. The change can be a movement, a deformation, or a rotation without any limitations. Please refer to FIG. 3A and FIG. 3B. FIG. 3A and FIG. 3B illustrate the user controlling the samples in the portable biochemical testing apparatus 1 through a touch way.

As shown in FIG. 3A, the sample displayed by the display module 15 of the portable biochemical testing apparatus 1 originally locates at a first position P. When a finger F of the user moves from the first position P to a second position P' shown in FIG. 3B, the portable biochemical testing apparatus 1 will use the above-mentioned mechanisms to control the sample to move to the second position P' correspondingly.

Therefore, the user can easily control the samples disposed in the portable biochemical testing apparatus 1 through the touch way.

It should be noticed that a display module 15 can be disposed above a top surface of the sample module 10, and used to display the samples disposed under the display module 15; the touch module 16 can be disposed above the top surface of the sample module 10 and the touch module 16 can overlap the display module 15. If a sample is located at a first sample position of the sample module 10, the sample will be displayed at the first display position of the display module 15 corresponding to the first sample position of the sample module 10. The touch module 16 can generate a touch command according to a touch action of an object (e.g., the finger F) touching a first touch position P of the touch module 16 overlapping the first display position P of the display module 15 above the sample module 10 and moving to a second touch position P' of the touch module 16 overlapping a second display position P' of the display module 15 above the sample module 10. The sample will be moved from the first sample position of the sample module 10 to a second sample position of the sample module 10 corresponding to the second display position P' of the display module 15. In addition, the track and direction of the sample moving from the first sample position of the sample module 10 to the second sample position of the sample module 10 overlap the track and direction of the object F moving from the first touch position P of the touch module 16 to the second touch position P' of the touch module 16.

Figure 4A:
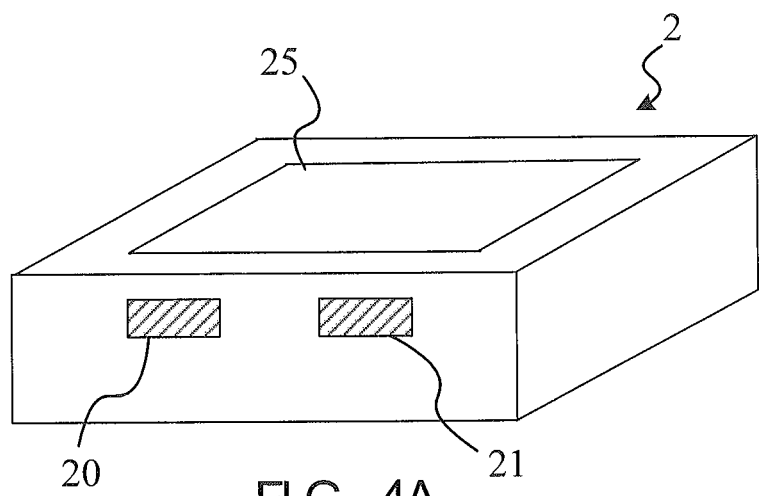
FIG. 4A and FIG. 4B illustrate different types of portable biochemical testing apparatuses.
Figure 4B:
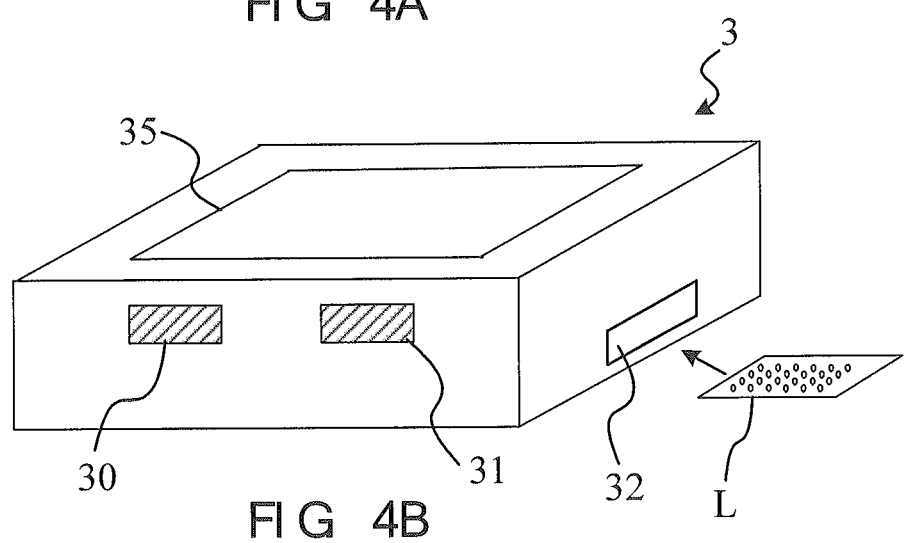

It should be noticed that the portable biochemical testing apparatus of the invention can also include a plurality of sample modules to dispose different samples respectively. As shown in FIG. 4A, the portable biochemical testing apparatus includes two sample modules 20 and 21 to dispose different samples, so that various samples can be tested at the same time. In addition, as shown in FIG. 4B, the light source module 32 of the portable biochemical testing apparatus 3 can be designed as a cassette-type for the user to change different light source units L. In fact, the light source module 32 can include changeable light source unit or a multi-band light source unit, but not limited to this case.

Figure 5A:
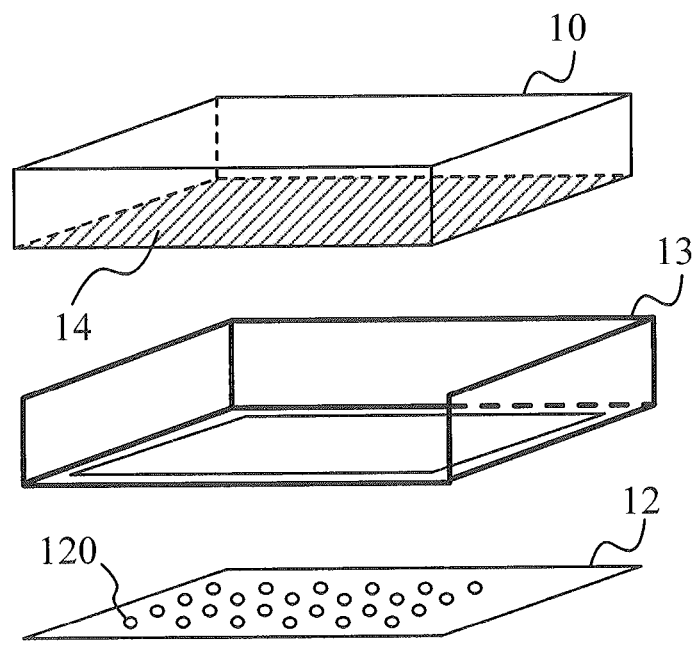
FIG. 5A and FIG. 5B illustrate the photoconductive material layer integrated with the sample module or the bearing module.
Figure 5B:
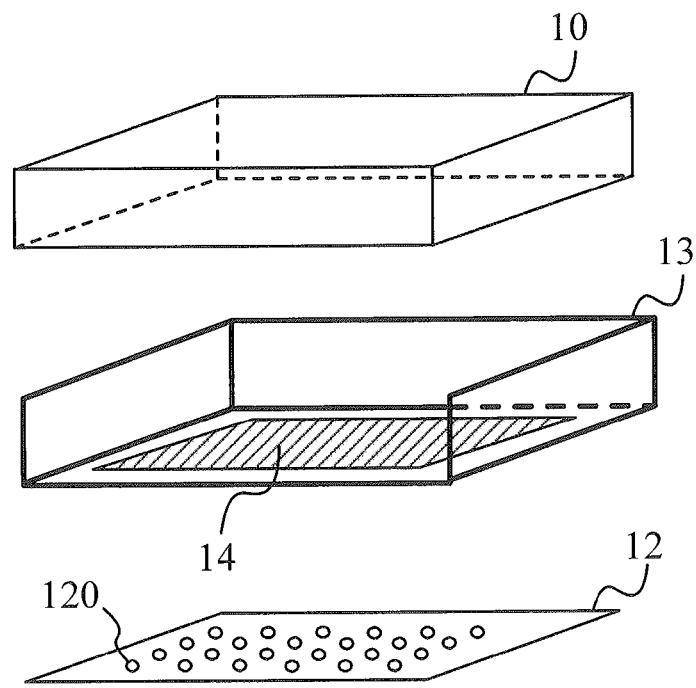

It should be noticed that in practical applications, the photoconductive material layer 14 of the invention can be integrated with different modules of the portable biochemical testing apparatus 1 through different designs. For example, as shown in FIG. 5A, the photoconductive material layer 14 can be directly integrated with the sample module, and the photoconductive material layer 14 is disposed under the samples. By doing so, the removable sample module 10 can be integrated with the photoconductive material layer 14 to provide the functions of bearing samples and driving samples at the same time. As to the bottom surface of the bearing module 13, it can be the hollow form as shown in FIG. 5A, or even the bearing module 13 can only remain side surfaces and include no bottom surface. In addition, as shown in FIG. 5B, the photoconductive material layer 14 is disposed under the sample module 10. The photoconductive material layer 14 can be integrated with the bearing module 13, and can be replaced by photoconductive material layers having different photoconductive characteristics, but not limited to this case.

Another embodiment of the invention is a portable biochemical testing apparatus operating method. In this embodiment, the portable biochemical testing apparatus operating method is applied in a portable biochemical testing apparatus to perform a procedure of test and observation to at least one sample. In fact, the at least one sample can be any kinds of biological samples or chemical samples without any limitations.

In this embodiment, the portable biochemical testing apparatus includes a light source module, a sample module, a photoconductive material layer, a touch module, and a control module, wherein at least one sample is disposed in the sample module, and the photoconductive material layer is disposed between the sample module and the light source module.

Figure 6:
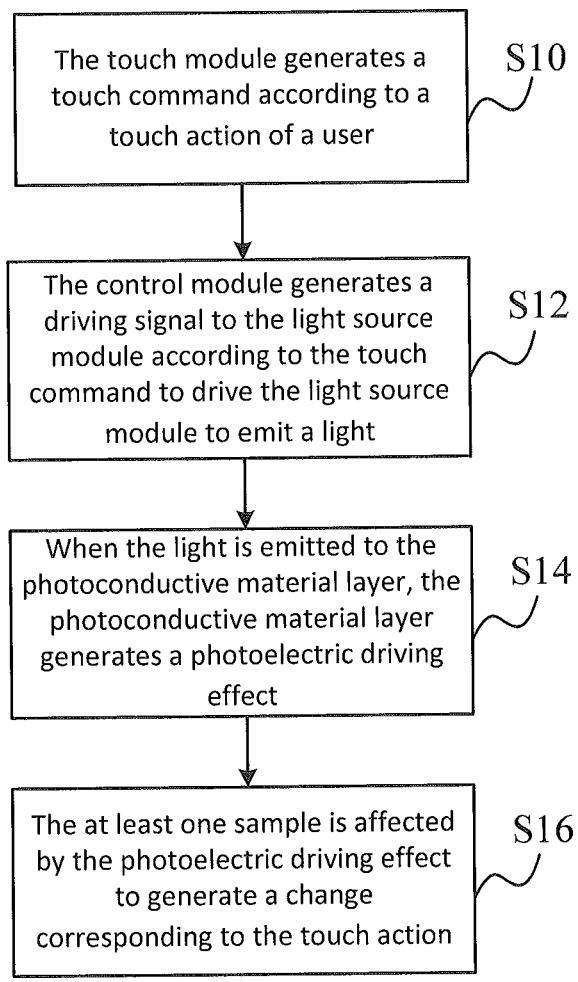
FIG. 6 illustrates a flowchart of the portable biochemical testing apparatus operating method of another embodiment in the invention.

Please refer to FIG. 6. FIG. 6 illustrates a flowchart of the portable biochemical testing apparatus operating method. As shown in FIG. 6, the portable biochemical testing apparatus operating method includes following steps. At first, in step S10, the touch module generates a touch command according to a touch action of a user. In practical applications, the portable biochemical testing apparatus can further include a display module. The touch module can include an image sensing unit. The image sensing unit is used to sense the touch action of the user generated on the display module and generate the touch command accordingly. In fact, the touch action can be a touch, a movement, a rotation, a dragging, or any other types of action.

Then, in step S12, the control module generates a driving signal to the light source module according to the touch command to drive the light source module to emit a light. In practical applications, the light source module can include a plurality of light source units. The plurality of light source units can be any types of light source emitting apparatuses, such as conventional bulbs, fluorescents, or LEDs, and the number and the positions of the light source units can be determined based on practical needs without any limitations. In addition, the control module can also generate corresponding driving signals to the light source module according to different touch commands to make a part of light source units or all light source units in the light source module to light.

In step S14, when the light is emitted to the photoconductive material layer, the photoconductive material layer generates a photoelectric driving effect. In practical applications, the photoelectric driving effect can be an electrophoresis (EP) mechanism, a dielectrophoresis (DEP) mechanism, or any other mechanisms of providing electric field change and/or magnetic field change through electrodes.

Afterward, in step S16, the at least one sample is affected by the photoelectric driving effect to generate a change corresponding to the touch action. In practical applications, as the above-mentioned DEP mechanism used to control the small substance, the at least one sample will be affected by the EP mechanism or the DEP mechanism to generate the change. The change can be a movement, a deformation, or a rotation without any limitations.

In practical applications, the photoconductive material layer can be integrated with different modules of the portable biochemical testing apparatus through different designs. For example, the photoconductive material layer can be directly integrated with the sample module, and the photoconductive material layer is disposed under the at least one sample. By doing so, the removable sample module can be integrated with the photoconductive material layer to provide the functions of bearing samples and driving samples at the same time.

In addition, the portable biochemical testing apparatus can further include a bearing module disposed between the sample module and the light source module. At this time, the photoconductive material layer can be integrated with the bearing module, and the photoconductive material layer is disposed under the sample module. By doing so, since the photoconductive material layer is not directly integrated with the sample module, the photoconductive material layer can be replaced based on practical needs. For example, the photoconductive materials having different photoconductive characteristics can be attached onto the bearing module, but not limited to this case.

In practical applications, the at least one sample disposed in the sample module is disposable or cleanable. Each of the at least one sample disposed in the sample module can be replaced through the extraction way. In addition, the light source module can also include a changeable light source unit or a multi-band light source unit, but not limited to this case.

Compared to the prior arts, the portable biochemical testing apparatus operating method thereof in the invention can not only provide the user the effect of easy control and observation through the design of touch interface, but also effectively shrink the volume and size of the portable biochemical testing apparatus through the photoelectric driving theorem, so that the user can carry or move the portable biochemical testing apparatus more easily. In addition, the removable sample module of the portable biochemical testing apparatus of the invention can be intergratedly designed with the photoconductive material layer, so that it can provide a sample bearing function and a sample driving function at the same time. Furthermore, the portable biochemical testing apparatus of the invention can test many sample modules at the same time, and provide the functions of changeable light source and multi-band light source.

Above all, the portable biochemical testing apparatus operating method thereof in the invention can effectively solve the problems of the conventional biochemical testing apparatus including being large and weighty, hard to be carried and moved, small sample observation field, hard to be controlled for the user, therefore, it has great market potential in the future.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. A method of operating a portable biochemical testing apparatus, the portable biochemical testing apparatus comprising a light source module, a sample module, a photoconductive material layer, a display module, a touch module, and a control module, at least one sample being disposed in the sample module, a specific sample of the at least one sample being located at a first sample position of the sample module, the photoconductive material layer being disposed between the sample module and the light source module, the display module being disposed above a top surface of the sample module and used to display the at least one sample disposed under the display module, the specific sample being displayed at a first display position of the display module corresponding to the first sample position of the sample module, the touch module being disposed above the top surface of the sample module and overlapping the display module, the method comprising steps of:

(a) the touch module generating a touch command according to a touch action of an object touching a first touch position of the touch module overlapping the first display position of the display module above the sample module and moving to a second touch position of the touch module overlapping a second display position of the display module above the sample module;
(b) the control module generating a driving signal to the light source module according to the touch command to drive the light source module to emit a light;
(c) when the light is emitted to the photoconductive material layer, the photoconductive material layer generating a photoelectric driving effect; and
(d) the photoelectric driving effect affecting the specific sample to move from the first sample position of the sample module to a second sample position of the sample module corresponding to the second display position of the display module.

2. The method of claim 1, wherein the photoconductive material layer and the sample module are integratedly designed, and the photoconductive material layer is disposed under the at least one sample.

3. The method of claim 1, wherein the portable biochemical testing apparatus further comprises a bearing module, the bearing module is disposed between the sample module and the light source module and used for bearing the sample module, the photoconductive material layer and the bearing module are integratedly designed, and the photoconductive material layer is disposed under the sample module.

4. The method of claim 1, wherein the at least one sample disposed in the sample module is disposable or cleanable, the sample module replaces each of the at least one sample respectively through an extraction way.

5. The method of claim 1, wherein the light source module comprises a changeable light source unit or a multi-band light source unit, and the photoelectric driving effect is an electrophoresis mechanism or a dielectrophoresis mechanism.

* * * * *